United States Patent
Ley et al.

(10) Patent No.: US 6,723,073 B2
(45) Date of Patent: *Apr. 20, 2004

(54) HEMOSTASIS VALVE FOR USE WITH A LEFT VENTRICULAR PACING LEAD

(75) Inventors: Gregory R. Ley, Blaine, MN (US); Bruce A. Tockman, Scandia, MN (US); Randy W. Westlund, Minneapolis, MN (US); David L. White, Little Canada, MN (US)

(73) Assignee: Cardiac Pacemakers, Inc., St. Paul, MN (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 10/236,309

(22) Filed: Sep. 6, 2002

(65) Prior Publication Data

US 2004/0049158 A1 Mar. 11, 2004

(51) Int. Cl.[7] .............................................. A61M 5/178
(52) U.S. Cl. ........................... 604/167.01; 604/167.04; 604/167.06; 604/167.02
(58) Field of Search ................................. 604/256, 161, 604/167, 171, 244, 167.01, 167.02, 166.01, 167.03, 167.04, 167.06, 246, 415, 905

(56) References Cited

U.S. PATENT DOCUMENTS

| | | | |
|---|---|---|---|
| 5,520,655 | A | 5/1996 | Davila et al. |
| 5,538,505 | A | 7/1996 | Weinstein et al. |
| 5,591,137 | A | 1/1997 | Stevens |
| 5,599,305 | A | 2/1997 | Hermann et al. |
| 5,643,227 | A | 7/1997 | Stevens |
| 5,693,025 | A | 12/1997 | Stevens |
| 5,935,112 | A | 8/1999 | Stevens et al. |
| 6,024,729 | A | 2/2000 | Dehdashtian et al. |
| 6,083,207 | A | 7/2000 | Heck |
| 6,086,570 | A | 7/2000 | Aboul-Hosn et al. |
| 6,088,889 | A | 7/2000 | Luther et al. |
| 6,142,981 | A | 11/2000 | Heck et al. |
| 6,352,520 | B1 | 3/2002 | Miyazaki |

*Primary Examiner*—Brian L. Casler
*Assistant Examiner*—K. Sirmons
(74) *Attorney, Agent, or Firm*—Thomas J. Nikolai; Nikolai & Mersereau, P.A.

(57) ABSTRACT

A hemostasis valve for use in introducing an over-the-wire medical lead into a patient's vascular system comprises a housing with a passageway, the passageway including an elastomeric pierceable seal member interposed therein and a resilient, annular tip surrounding a distal end of the housing where the tip has a central opening that is sized to receive a tubular connector terminal at the proximal end of the medical lead for dripping the end of the lead and sealing the lead's tubular connector terminal in the passageway of the housing.

8 Claims, 2 Drawing Sheets

HEMOSTASIS VALVE FOR USE WITH A LEFT VENTRICULAR PACING LEAD

BACKGROUND OF THE INVENTION

I. Field of the Invention

This invention relates generally to apparatus for facilitating placement of an over-the-wire, left ventricular lead in a patient, and more particularly to a hemostasis valve for creating a fluid-tight seal with a proximal lead terminal of a left ventricular pacing lead and with a guidewire used during a lead implant procedure.

II. Discussion of the Prior Art

In treating heart failure patients with cardiac stimulation, it is necessary to install a stimulating/sensing lead on the left side of the heart. However, placement of the lead itself into the left ventricle is to be avoided. A procedure has been perfected for advancing a very small diameter lead through the coronary sinus and down a coronary vein on the left side of the heart whereby electrical stimulation of myocardial tissue of the left ventricle can be achieved. Because the lead must necessarily be of a small diameter and be highly flexible, it lacks steerability. Therefore, a guidewire is used to facilitate routing of the lead. The guidewire is advanced through the vascular system until its distal end enters the target coronary vein. The stimulating lead is tubular in configuration, allowing it to be slipped over the guidewire and advanced by pushing until its distal electrode(s) are at a desired location on the left ventricle.

In that the lead is tubular, blood can flow through its lumen and if clotting occurs, it may prove difficult to extract the guidewire without dislodging the lead. If blood is allowed to exit the proximal end of the lead, it can create a mess for the surgeon or cardiologist to deal with.

Accordingly, there is a need for a hemostasis valve that can be used to prevent blood or other fluid loss during lead implant procedures involving over-the-wire cardiac stimulating leads and which can be used to prevent clotting in the lumen of the lead.

The prior art discloses a variety of catheter introducers incorporating hemostasis valves, whereby blood loss along the outside diameter of a guidewire or diagnostic or angioplasty catheter is prevented. The Stevens U.S. Pat. Nos. 5,693,025 and 5,935,112 are exemplary. They each include a resilient rubber seal member having an aperture therethrough for receiving a guidewire and a collar that when screwed down on the proximal end of the device compresses the seal member tightly against the guidewire. A further collet-like clamp is provided at the distal end of the Stevens' introducer to provide a way of clamping the device in place on a proximal end of a catheter. The introducer of the prior art Stevens patent also includes provision for introducing a fluid or some other medical device into the patient's body.

U.S. Pat. No. 6,142,981 to Heck et al. describes a cannula having a hemostasis valve thereon that incorporates an elastomeric seal having a self-closing aperture which, when forced open by a guidewire or the like, seals about the guidewire to prevent blood loss therealong. No provision is made for clamping the distal end of the cannula to a catheter or stimulating lead. Thus, the device described in the Heck '981 patent is similar in most respects to the hemostasis cannula valve described in the Stevens U.S. Pat. No. 5,643,227 and the Davila et al. U.S. Pat. No. 5,520,655.

SUMMARY OF THE INVENTION

The present invention is directed to a hemostasis valve for use in introducing an over-the-wire medical lead into a subject's vascular system. An over-the-wire lead comprises a lead body with a distal end, a proximal end and a lumen that extends between the two ends. Affixed to the proximal end of the lead body is a tubular connector terminal that is adapted to mate with contacts in the header of a cardiac rhythm management device, such as a pacemaker or defibrillator. The hemostasis valve itself comprises a molded plastic housing having a passageway therein with first and second openings in communication with the passageway. An elastomeric, pierceable, seal member is carried by the housing for sealing the first opening. A resilient annular tip surrounds the second opening and it itself has a central opening sized to receive the tubular connector terminal at the proximal end of the lead body therein with a predetermined friction fit for both gripping and sealing the tubular connector terminal with respect to the housing. This design obviates the need for a screw-type clamp at opposed ends of the housing, one for establishing a seal to the guidewire and the other for establishing a seal to the lead's tubular connector terminal.

DESCRIPTION OF THE DRAWINGS

The foregoing features, objects and advantages of the invention will become apparent to those skilled in the art from the following detailed description of a preferred embodiment, especially when considered in conjunction with the accompanying drawings in which like numerals in the several views refer to corresponding parts.

DESCRIPTION OF THE PREFERRED EMBODIMENT

Figure 1:
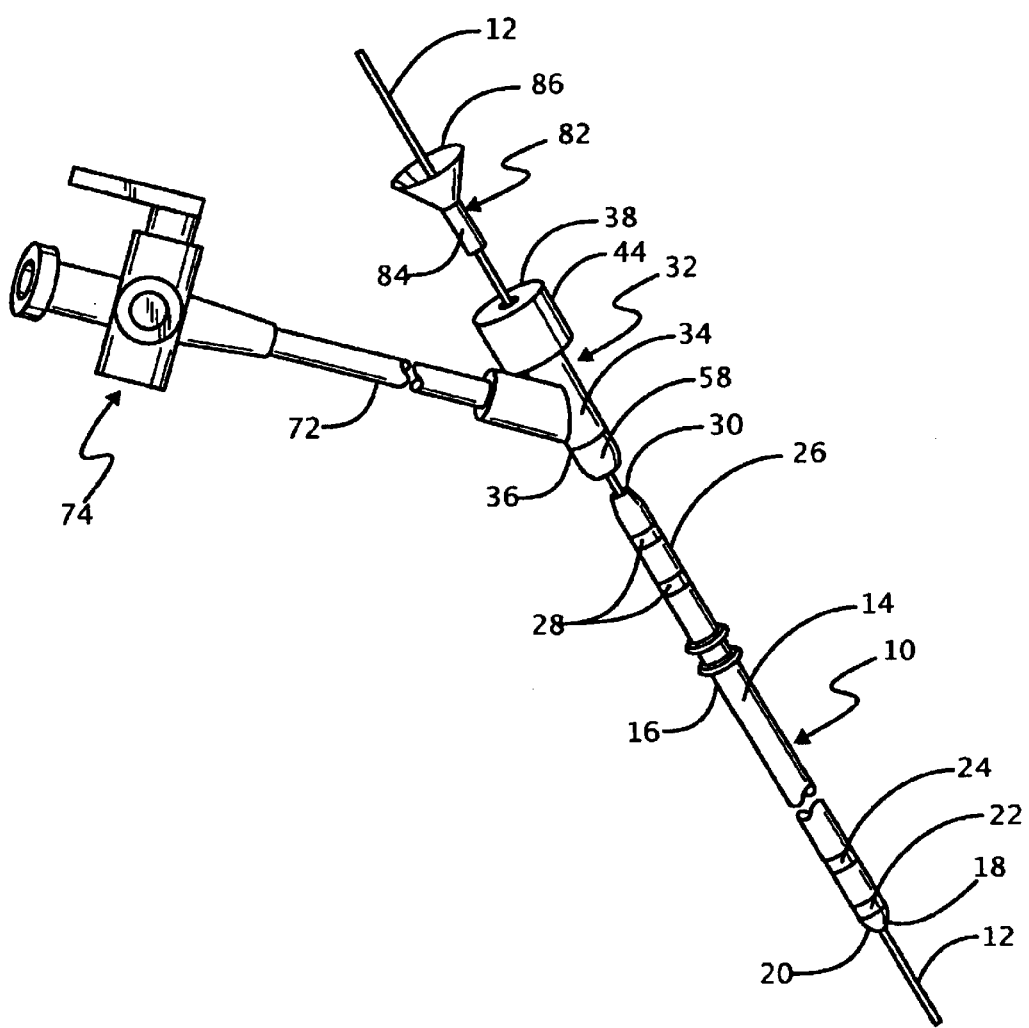
FIG. 1 is an exploded perspective view showing an over-the-wire pacing lead assembled on to a guidewire and the hemostasis valve assembly comprising a preferred embodiment of the present invention.

Referring to FIG. 1, there is shown an over-the-wire cardiac stimulating lead 10 disposed on an elongated guidewire 12. The lead 10 includes an elongated flexible elastomeric lead body 14 having a proximal end 16, a distal end 18 and a lumen 20 that extends all the way from the proximal end to the distal end. One or more electrodes as at 22 and 24 are provided on the surface of the lead body 14 in a distal zone of the lead 10. Affixed to the proximal end 16 of the lead body 14 is a tubular lead connector terminal 26 which is adapted to be inserted into a connector bore in a header of a cardiac rhythm management device, such as a pacemaker or an automatic implantable cardiac defibrillator. The tubular connector 26 includes contacts, as at 28, that are connected by wires (not shown) that extend the length of the lead body and make an electrical connection to the electrodes 22 and 24 on the distal end portion of the lead. The tubular connector 26 is open at its proximal end 30 allowing the guidewire 12 to pass through the connector terminal 26, down the length of the lead body 14 and out its distal opening 20.

Figure 2:
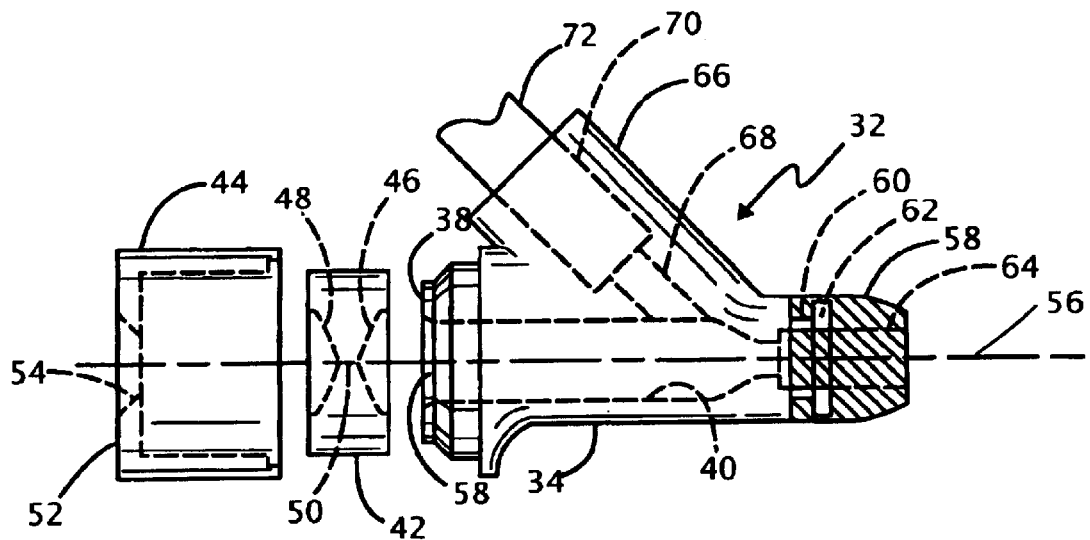
FIG. 2 is an enlarged side elevational view of the hemostasis valve assembly without the side port three-way stopcock.

With continued reference to FIG. 1, it is seen there that there is also a hemostasis valve assembly that is indicated generally by numeral 32. It comprises a molded plastic housing 34 having a distal end 36 and a proximal end 38. The housing 34 defines a passageway 40 (FIG. 2) from one end to the other. An elastomeric seal member 42 is contained within a proximal cap 44 that is bonded to the proximal end 38 of the housing 34, preferably in an ultrasonic welding operation.

The seal 42 comprises a cylindrical block of elastomeric material having opposed conically shaped recesses 46 and 48 formed inwardly and with a fine pinhole 50 extending between the apices of the opposed conical recesses 46 and 48. The proximal end cap 44 has a top surface 52 with a frustoconical aperture 54 formed therethrough in general alignment with the recesses 46 and 48 which lie on a longitudinal axis of the assembly 32. It can be seen, then, that when the cap 44 containing the elastomeric seal member 42 is joined to the body member 34, the elastomeric seal 42 blocks the opening 58 at a first end of the passageway 40 through the housing 34.

Without limitation, the seal member 42 may be fabricated from polyisoprene and because of the self-closing pinhole 50 formed therein, the guidewire 12 may readily penetrate through the seal member with the polyisoprene material forming a lip seal against the guidewire preventing the flow of blood or saline beyond the seal element.

Over molded onto the polycarbonate housing 34 is a resilient annular tip, preferably, but not necessarily, formed of polyurethane. The resilient annular tip is identified by numeral 58 in FIGS. 1 and 2. In order to positively retain the over-molded resilient annular tip 58 on the housing 34, an annular groove 60 is formed inwardly from the exterior surface thereof to create a flange 62. When the polyurethane tip 58 is over-molded onto the distal end of the housing 34, it flows into the groove 60 and about the flange 62. The inner diameter of the bore 64 in the annular polyurethane tip 58 is designed to be slightly less than the outside diameter of the tubular connector terminal 26 with which the hemostatic valve 32 is used. Thus, the annular tip member 58 not only clamps on to the proximal end of the tubular connector terminal when it is forced into the bore 64, but the close fit also creates a fluid-tight seal about the outer surface of the tubular connector terminal 26.

Figure 3:
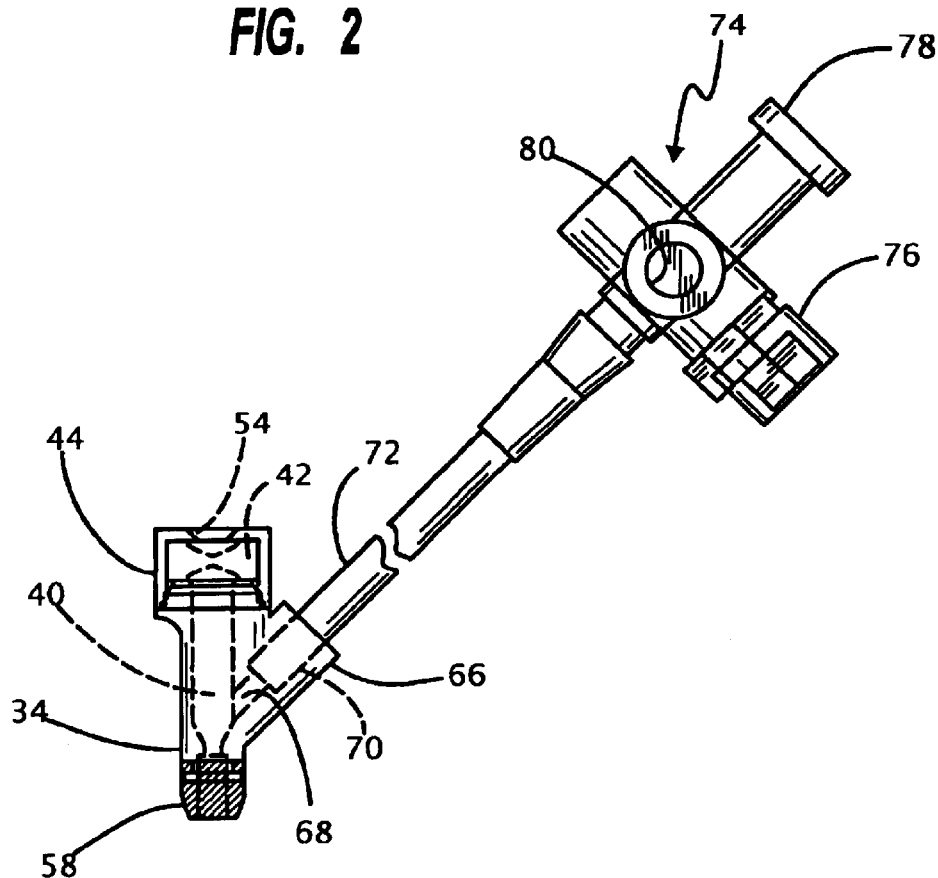
FIG. 3 is an exploded side elevational view of the hemostasis valve assembly.

Integrally formed with the housing 34 is a Y-branch 66 having a bore 68 comprising a flushing port that is in fluid communication with the passageway 40 and a counterbore 70. Referring to FIG. 3, there is shown a length of plastic tubing 72 fitted into the counterbore 70. Attached to the other end of the tube 72 is an outlet port of a three-way stop-cock assembly indicated generally by numeral 74. The stop-cock assembly has an actuating lever 76 for rotating a ball valve member (not shown) where that ball valve member has two radial bores formed that intersect therethrough at a right angle. A lure fitting 78 comprising a first inlet port allows the stop-cock assembly to be coupled to a fluid-filled syringe (not shown). When the lever 76 is turned, such that one bore in the ball valve is longitudinally aligned with the lure fitting 78 and the tube 72, a flushing fluid can be ejected from the syringe, through the tube 72 and the bore 68 into the passageway 40 leading to the lumen in the lead terminal connector 26 and the lumen in the lead body 14 itself.

When the stop-cock lever is rotated 90°, a second inlet port 80 is made to be in fluid communication with the tube 72 so that a second fluid, for example, an anti-coagulant, can be introduced into the fluid that is made to pass through the hemostatic valve assembly and the lead, thereby inhibiting clotting that might otherwise make it difficult to remove the guidewire 12 from the lead without displacing the electrodes 22 and 24 on the lead from their target location on the left side of the heart.

It can be seen, then, that the hemostasis valve of the present invention is indicated for maintaining a seal around the terminal connector of a lead at the distal end of the valve assembly and around a guidewire at the proximal end during lead lumen flushing and implant procedures. To facilitate penetration of the elastomeric seal member 42 by the supple tip of an atraumatic guidewire, there is also provided a wire guide member 82 (FIG. 1). The wire guide member 82 is funnel-shaped, having a tubular stem 84 and a cone-shaped head 86 at its proximal end. The wire guide member 82 is preferably molded from a medical-grade plastic and is relatively rigid. As such, the tubular stem 84 thereof may be forced through the pinhole slit 50 in the seal member 42 and the funnel head 86 acts to direct the tip of the guidewire through the wire guide member into the passage 40 of the hemostatic valve assembly 32 and from there, down the lumen of the lead.

It can be seen, then, that by this invention there is provided a hemostasis seal that allows movement of a guidewire into and out of the vasculature, catheter and lead lumen with substantially no fluid loss. The seal assembly also allows for easy penetration and introduction of the wire guide member 82 through the seal which, in turn, accommodates the introduction of the floppy end of the guide wire through the wire seal. Moreover, sealing is achieved without the need to rotate an end cap as in prior art designs. Further, because of the design of the tip member 58, it is not necessary to provide a collet-type clamp to affix the hemostatic seal assembly to the lead's terminal pin.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself

What is claimed is:

1. A hemostasis valve for use in introducing an over-the-wire medical lead into a subject's vascular system, the lead having an elongated, flexible lead body with a distal end, a proximal end, a lumen extending therebetween and a tubular connector terminal at the proximal end of the lead body, the hemostasis valve comprising:

(a) a housing having a proximal end, a distal end and a passageway extending therebetween with first and second openings in communication with said passageway, said housing including an annular groove proximate the second opening;

(b) an elastomeric, pierceable seal member carried by the housing for sealing the first opening; and (c) an elastomeric resilient annular tip surrounding the second opening of the housing with a portion projecting into the annular groove, the resilient annular tip extending distally from the distal end of the housing, the tip having a central opening sized to receive the tubular connector terminal at the proximal end of the lead body therein with a predetermined friction fit for releasably elastically gripping and sealing the tubular connector terminal with respect to the housing.

2. The hemostasis valve as in claim 1 wherein the seal member includes a self-closing, pierceable aperture formed therethrough.

3. The hemostasis valve as in claim 2 and further including a means for facilitating insertion of a medical guide wire through the self-closing pierceable aperture and through the tubular connector terminal.

4. The hemostasis valve as in claim 3 wherein said means comprises a rigid tube having a conical funnel at a proximal end, the rigid tube adapted to be inserted through the pierceable aperture.

5. The hemostasis valve as in claim 1 wherein the housing further includes a flushing port in fluid communication with the passageway between the seal member and the elastomeric annular tip.

6. The hemostasis valve as in claim 5 and further including means for injecting a flushing fluid into the passageway.

7. The hemostasis valve as in claim 6 wherein the means for injecting a flushing fluid into the passageway comprises a three-way stop-cock having first and second inlet ports and an outlet port, the outlet port being coupled to the flushing port of the hemostasis valve.

8. The hemostasis valve as in claim 1 wherein the elastomeric annular tip is made of polyurethane.

* * * * *